(12) United States Patent
Choi et al.

(10) Patent No.: US 7,450,002 B2
(45) Date of Patent: Nov. 11, 2008

(54) METHOD AND APPARATUS FOR MONITORING HUMAN ACTIVITY PATTERN

(75) Inventors: Ji-hyun Choi, Seoul (KR); Kun-soo Shin, Seongnam-si (KR); Jin-sang Hwang, Suwon-si (KR); Hyun-tai Hwang, Yongin-si (KR); Wan-taek Han, Hwasgong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 284 days.

(21) Appl. No.: 11/332,586

(22) Filed: Jan. 17, 2006

(65) Prior Publication Data
US 2006/0161079 A1    Jul. 20, 2006

(30) Foreign Application Priority Data
Jan. 14, 2005  (KR) .............. 10-2005-0003635

(51) Int. Cl.
*G08B 1/08* (2006.01)
*H04Q 7/00* (2006.01)
*A61B 5/103* (2006.01)
*A61B 5/117* (2006.01)

(52) U.S. Cl. ................ 340/539.11; 340/573.1; 340/573.4; 340/686.1; 600/595

(58) Field of Classification Search ............ 340/539.11, 340/573.1, 539.12, 539.13, 539.15, 539.26, 340/573.4, 686.1, 689; 600/587–595
See application file for complete search history.

(56) References Cited

U.S. PATENT DOCUMENTS

| | | | |
|---|---|---|---|
| 7,028,547 B2* | 4/2006 | Shiratori et al. | 73/495 |
| 7,127,370 B2* | 10/2006 | Kelly et al. | 702/151 |
| 2006/0052727 A1* | 3/2006 | Palestrant | 600/595 |
| 2006/0161079 A1* | 7/2006 | Choi et al. | 600/595 |
| 2006/0255955 A1* | 11/2006 | O'Connor et al. | 340/573.1 |

* cited by examiner

*Primary Examiner*—Toan N Pham
(74) *Attorney, Agent, or Firm*—Sughrue Mion, PLLC (57) ABSTRACT

A method and apparatus for monitoring a human activity pattern irrespective of the wearing position of the sensor unit by a user and a direction of the sensor unit are provided. The method for monitoring an inertia movement signal according to a movement of a user using a sensor unit attached to the user; detecting a direction of the sensor unit from the inertia movement signal; detecting a wearing location of the sensor unit by using acceleration and direction; determining the activity pattern of the user from inertia sensors; and delivering physical activity data corresponding to at least one caloric consumption, number of steps, and movement distance.

17 Claims, 8 Drawing Sheets

METHOD AND APPARATUS FOR MONITORING HUMAN ACTIVITY PATTERN

CROSS-REFERENCE TO RELATED PATENT APPLICATIONS

This application claims the benefit of Korean Patent Application No. 10-2005-0003635, filed on Jan. 14, 2005, in the Korean Intellectual Property Office, the disclosure of which is incorporated herein in its entirety by reference.

BACKGROUND OF THE INVENTION

1. Field of the Invention

The present invention relates to a method and apparatus for monitoring human activity, and more particularly, to a method and apparatus for monitoring a human activity pattern to provide information on the amount of physical activity of a user by monitoring the caloric consumption of the user during daily activities.

2. Description of the Related Art

In order to maintain the healthy life of an individual, there is a need to continuously measure the amount of daily activity and caloric consumption without limiting the daily activities.

Among the technologies for monitoring the amount of daily activity are those disclosed in WO 96-30080 and U.S. Pat. No. 6,165,143. These patents disclose technologies for finding the activity pattern of an individual by using a variety of sensors, and measuring the amount of physical activity. However, these conventional technologies have restrictions such that in order to find the activity pattern of an individual, the direction and the location of a sensor must be fixed.

For example, in the WO 96-30080, a sensor is implanted in the heart, and the direction and location of the sensor are required to be fixed, and in U.S. Pat. No. 6,165,143 sensors are required to be attached at the waist, the upper leg, and the frontal points of knee joints.

SUMMARY OF THE INVENTION

The present invention provides a method and apparatus for monitoring a human activity pattern in which by using a 3-axis acceleration sensor and a terrestrial magnetism sensor, movement in the direction of gravity and movement in the horizontal direction by a user are separated. Further, by using the signal characteristics with respect to the locations of the sensor, the attached locations of the sensor can be recognized regardless of the directions of the sensor, and the activity pattern of the user can be determined.

According to an aspect of the present invention, there is provided a method for monitoring a human activity pattern including: sensing an inertia movement signal according to a movement of a user using a sensor unit attached to the user; detecting a direction of the sensor unit from acceleration; by using the inertia movement signal and direction, detecting a wearing location of the sensor unit; and determining the activity pattern of the user from the inertia movement signal by reflecting the wearing location.

According to another aspect of the present invention, there is provided an apparatus for monitoring a human activity pattern including: a sensor unit attached to a user, which senses an inertia movement signal according to a movement of the user; and a data processing unit which detects an acceleration signal and a direction signal of the sensor unit by using the inertia movement signal, detects a wearing location of the sensor unit by using the inertia movement signal and the direction, and determines the activity pattern of the user from the inertia movement signal by reflecting the wearing location.

According to still another aspect of the present invention, there is provided a computer readable recording medium having embodied thereon a computer program for executing the method for monitoring an activity pattern.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

Figure 1:
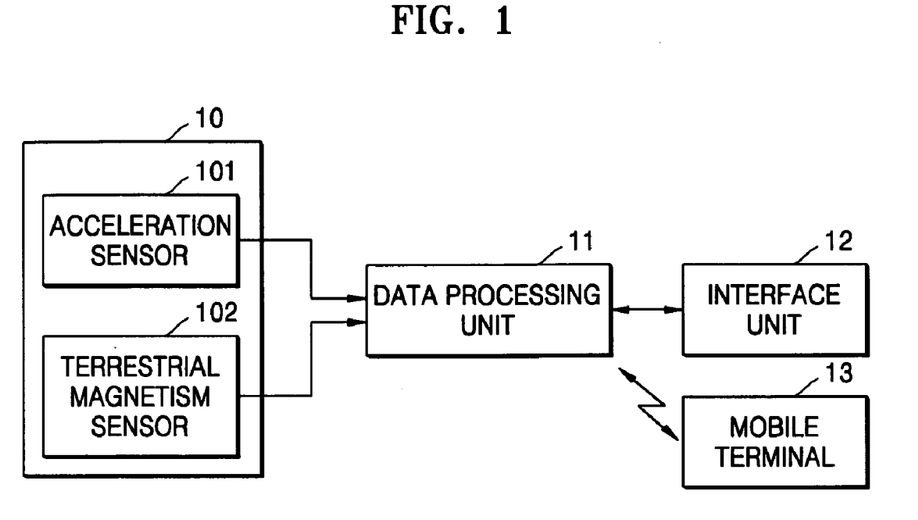
FIG. 1 is a block diagram of an apparatus for monitoring a human activity pattern according to an exemplary embodiment of the present invention.

Referring to FIG. 1, an apparatus for monitoring a human activity pattern includes a sensor unit 10 and a data processing unit 11.

Also, the apparatus for monitoring a human activity pattern may further include an interface unit 12 for providing results processed in the data processing unit to a user, or receiving required inputs from the user, and a mobile terminal 13 which operates in the same manner as the interface unit 12 does, but is wirelessly connected. In addition, according to another exemplary embodiment, the apparatus for monitoring a human activity pattern may be implemented as a separate apparatus, or may be embedded in the mobile terminal 13. In the latter case, the interface unit 12 can be implemented as a display panel or a keypad located on the mobile terminal 13.

The mobile terminal, may be capable of wireless communication, and may be a personal digital assistant (PDA), a portable computer, or a mobile phone. The mobile terminal may communicate in a short range wireless communication scheme such as Bluetooth, and/or may communicate through a cable such as a USB port or RS232C.

The sensor unit 10 includes a 3-axis acceleration sensor 101 for measuring an inertia movement, more specifically, acceleration in x, y, and z directions, and may further include a terrestrial magnetism sensor 102 or gyroscope (not shown) for detecting the orientation of the sensor unit 10 with respect to a planar surface parallel to the sensor unit 10. Also, in order to sense the orientation of the sensor unit 10 with respect to the planar surface, a tilt sensor for measuring the tilt from a reference vertical axis may further be included.

The data processing unit 11 processes an acceleration signal output from the acceleration sensor 101 to measure an acceleration value in relation to vibration in the 3-axis directions or an external acceleration value such as gravity, and processes the direction signal output from the terrestrial magnetism sensor 102. While detailed descriptions pertaining to the signal processed by the data processing unit 11 are limited to the acceleration signal, one of ordinary skill will appreciate that in other exemplary embodiments the signal can be extended more broadly to the inertia movement signal.

Also, the data processing unit 11 transforms the measured acceleration values and direction signal in the body frame of the sensor unit 10 into the ones of the space fixed coordinates.

Figure 2:
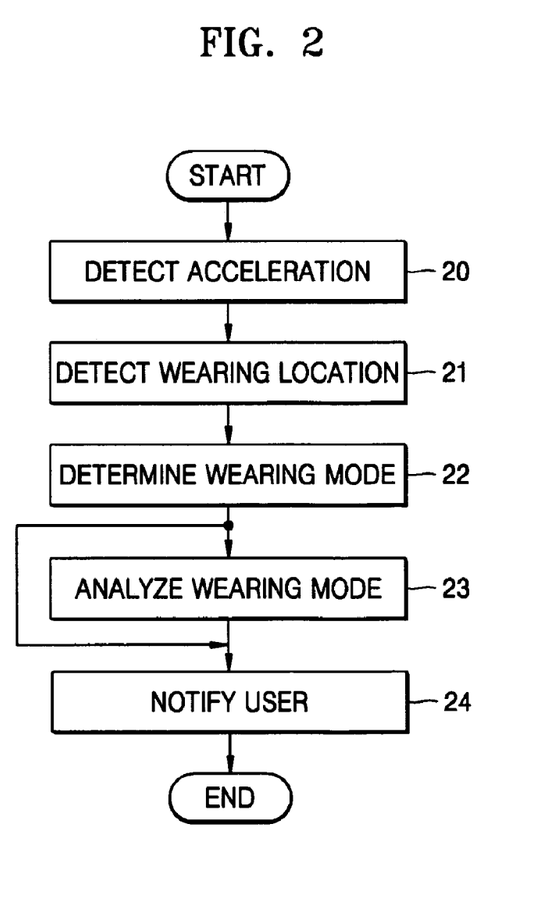
FIG. 2 is a flowchart of the operations performed by a method for monitoring a human activity pattern according to an exemplary embodiment of the present invention.

FIG. 2 is a flowchart of the operations performed by a method for monitoring a human activity pattern according to the present invention.

First, the data processing unit 11 detects the direction of the sensor unit 10 from the DC component of the acceleration sensor 101, and after compensating the acceleration of the AC component output from the acceleration sensor 101 for the direction of the sensor unit 10, outputs the compensated result in operation 24.

Figure 3:
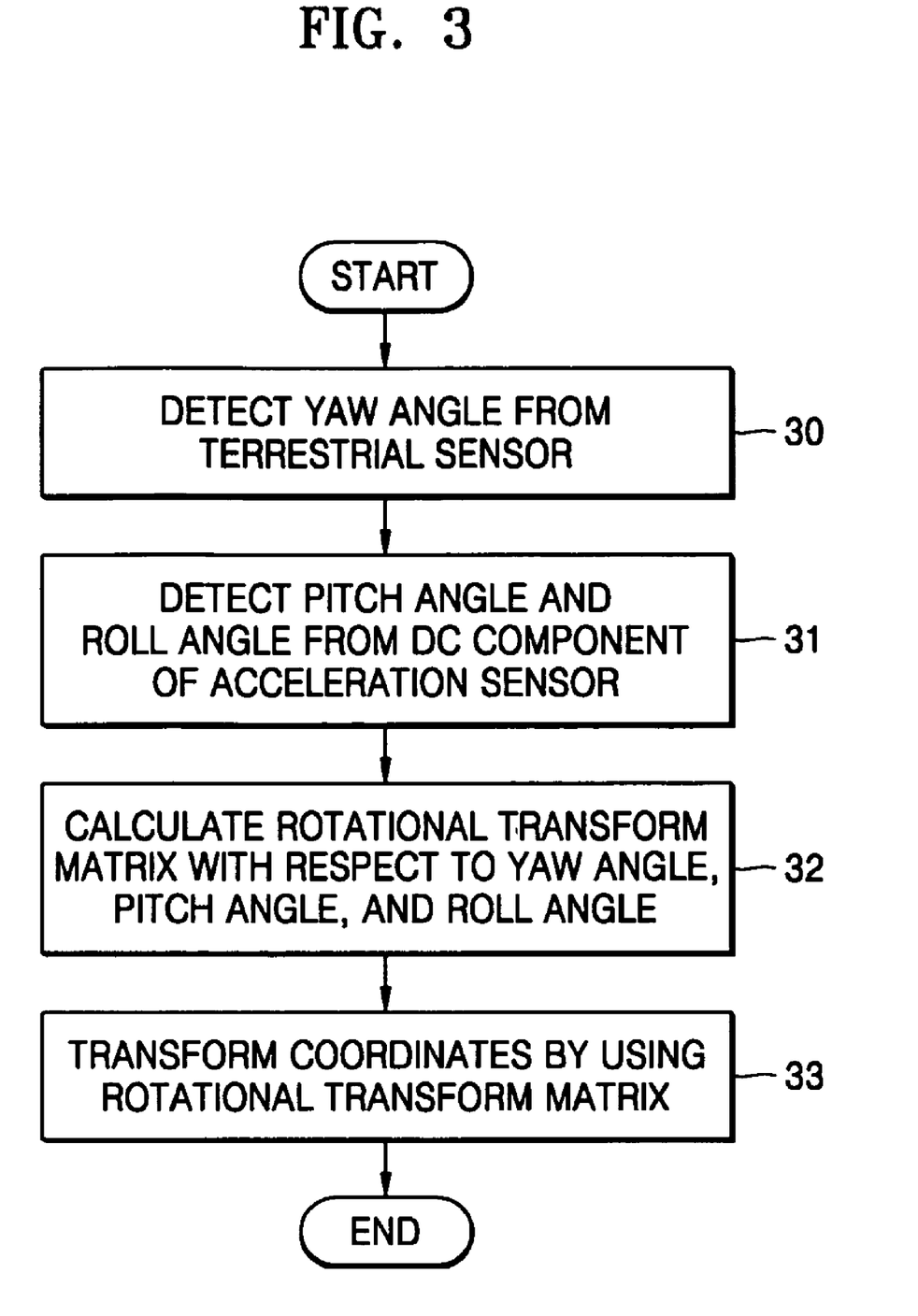
FIG. 3 is a detailed flowchart illustrating a process for detecting a direction.

FIG. 3 is a flowchart of the operations performed in an exemplary process for detecting direction.

Figure 4A:
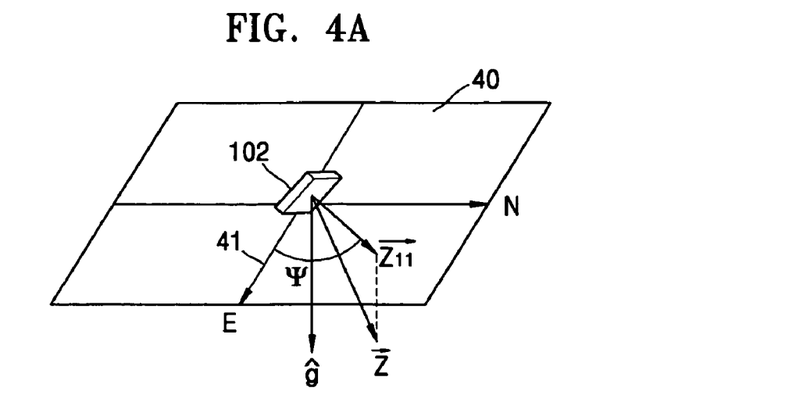
FIG. 4A illustrates a principle of measuring a yaw angle using a terrestrial magnetism sensor.

First, a yaw angle ψ is detected by using the terrestrial magnetism sensor 102 in operation 30. The yaw angle is not necessarily needed for detecting the direction of the sensor unit 10, but is a useful component. FIG. 4A illustrates the principle of measuring a yaw angle by using the terrestrial magnetism sensor 102. Referring to FIG. 4A, when the terrestrial magnetism sensor 102 is tilted with respect to the planar surface 40, the yaw angle ψ indicates the angle that the terrestrial magnetism sensor 102 sweeps the planar surface 40 from the reference line 41 indicating the E-direction of the planar surface 40. When $\hat{g}$ denotes the gravity acceleration and $\vec{z}$ denotes the vector of the orientation of the terrestrial magnetism sensor 102, a vector $\vec{z}_{//}$ obtained by projecting $\vec{z}$ onto the planar surface 40 and the yaw angle ψ can be obtained through the following equation 1:

$$\vec{z}_{//} = \vec{z} - (\vec{z} \cdot \hat{g})\hat{g} \quad (1)$$

$$\cos(\Psi) = \frac{\vec{z}_{//} \cdot \hat{E}}{\sqrt{\vec{z}_{//} \cdot \vec{z}_{//}}}$$

Figure 4B:
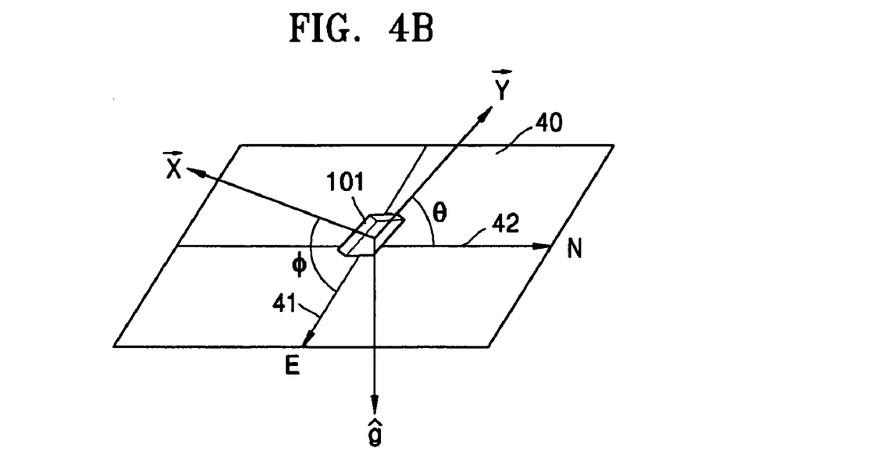
FIG. 4B illustrates a principle of obtaining a pitch angle and a roll angle using a DC component of acceleration.

The pitch angle θ and the roll angle Φ can be obtained from the DC component of an acceleration signal output from the acceleration sensor 101 or the tilt sensor in operation 31. FIG. 4B illustrates the principle of obtaining a pitch angle and a roll angle by using the DC component of acceleration.

Referring to FIG. 4B, the pitch angle θ indicates an angle from the reference line 42 to the Y-axis of the acceleration sensor 101, and the roll angle Φ indicates an angle from the reference line 41 to the X-axis of the acceleration sensor 101. The pitch angle θ and roll angle Φ can be obtained by the following equation 2:

$$\cos\left(\frac{\pi}{2} - \phi\right) = \frac{\vec{x} \cdot \hat{g}}{\sqrt{\vec{x} \cdot \vec{x}}} \quad (2)$$

$$\cos\left(\frac{\pi}{2} - \theta\right) = \frac{\vec{y} \cdot \hat{g}}{\sqrt{\vec{y} \cdot \vec{y}}}$$

If the yaw angle, pitch angle, and roll angle are obtained as shown in FIGS. 4A and 4B, a rotational transform matrix with respect to the yaw angle, pitch angle, and roll angle is obtained in operation 32. The rotational transform matrix may be obtained with respect to only the pitch angle and roll angle, or with respect to the yaw angle, pitch angle, and roll angle. The rotational transform matrix is multiplied by the AC component of the acceleration value output from the acceleration sensor 101. Thus, acceleration components in x, y, and z direction in the body frame of the acceleration sensor 101 are transformed into acceleration values in the space fixed coordinates in operation 33. Consequently, the acceleration values output from the data processing unit 11 are compensated for the direction of the sensor unit 10 to be output. At this time, if the acceleration is compensated for by using the rotational transform matrix containing the yaw angle, pitch angle, and roll angle, more accurate compensation can be performed than when using the rotational transform matrix containing only the pitch angle and roll angle, Using the acceleration value in the space fixed coordinates, the wearing location of the sensor unit 10 is detected in operation 21. The wearing location can be detected by a kinematics approach to human walking and pendulum modeling.

Figure 5:
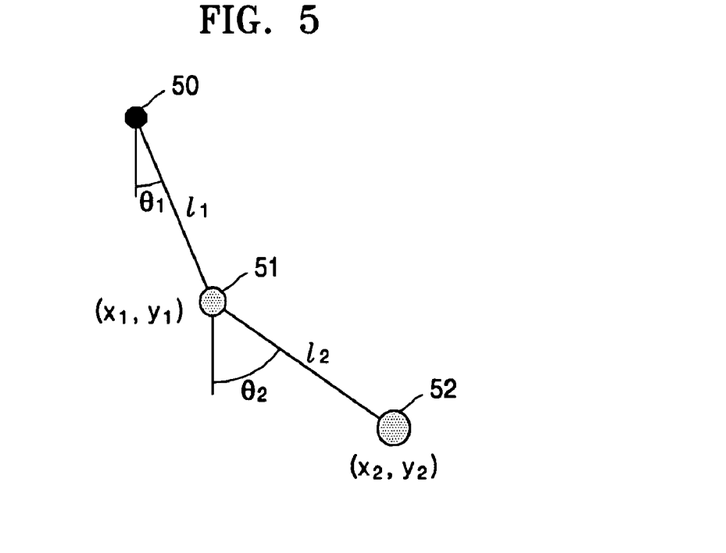
FIG. 5 illustrates a process for modeling a sensor attached to the body as a pendulum.

The kinematics approach focuses on the fact that when a person moves, a trajectory of a signal output from the sensor unit 10 varies depending on the wearing location. The pendulum modeling regards the sensor as attached to the human body as a pendulum, and models the movement trace of the sensor as shown in FIG. 5, to determine the characteristics of a signal which differ depending on the wearing location. That is, when the waist or the body is regarded as a fixed point, and the sensor unit 10 is located on the arm, hand, or leg, or in a pocket or handbag, the movement of the sensor unit 10 is modeled as a single or as a double pendulum movement.

Referring to FIG. 5, reference number 50 indicates the body of the fixed point, and reference number 51 indicates the sensor unit 10 modeled as the single pendulum when the sensor unit 10 is held in the hand or the pocket. Reference number 52 indicates the sensor unit 10 modeled as the second pendulum connected to the first pendulum while the arm is modeled as the first pendulum when the sensor unit 10 is put in the handbag.

If ($x_1$, $y_1$) denotes the location of the first pendulum 51, and ($x_2$, $y_2$) denotes the location of the second pendulum 52, then when the user moves, it can be regarded that the fixed point 50 moves horizontally at a speed of v. At this time, the location of each pendulum 51 and 52 can be obtained by the following equation 3:

$$x_1 = vt + l_1 \sin\theta_1$$
$$y_1 = -l_1 \cos\theta_1$$
$$x_2 = vt + l_1 \sin\theta_1 + l_2 \sin\theta_2$$
$$y_2 = -l_1 \cos\theta_1 - l_2 \cos\theta_2 \qquad (3)$$

Here, $l_1$ denotes the distance between the fixed point 50 and the first pendulum 51, and $l_2$ denotes the distance between the first pendulum 51 and the second pendulum 52.

Figure 6A:
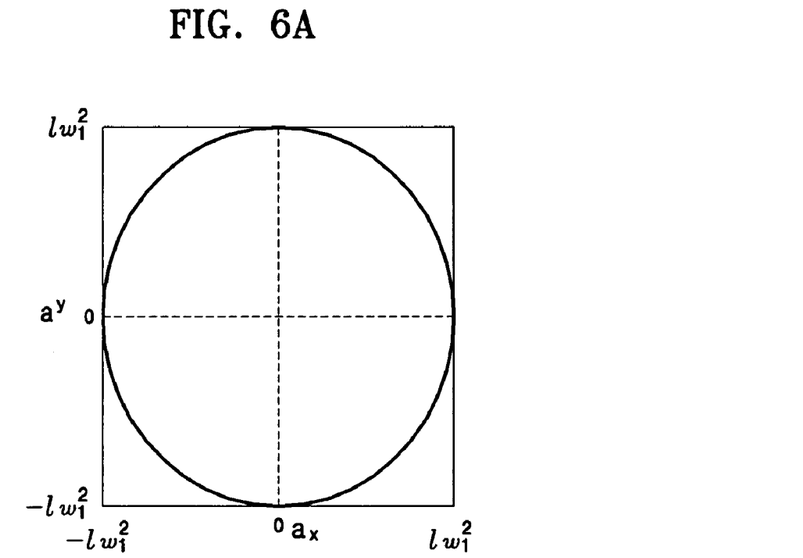
FIG. 6A is a phase diagram for the gravity direction and the horizontal direction components of acceleration, which is symmetric about the axis of the gravity direction component.

When the movement trajectory is modeled as a single pendulum, the acceleration signals in the gravity and horizontal directions show a phase diagram in the form of a circle as shown in FIG. 6A. At this time, with respect to the radius $l\psi^2$ of the circle, it is determined whether the sensor unit 10 is on the arm or leg, or in the pocket. That is, by referring to the distance between the fixed point 50 to the first pendulum 51 as the distance from the reference point of the body to the wearing location of the sensor unit 10, the location of the sensor unit 10 is determined from the radius of the circle.

At this time, the data processing unit can store in advance the distances, input through the interface unit 12, from the reference point to all the wearing locations at which the sensor unit 10 can be located, such as the arm, leg, pocket, and hand.

Figure 6B:
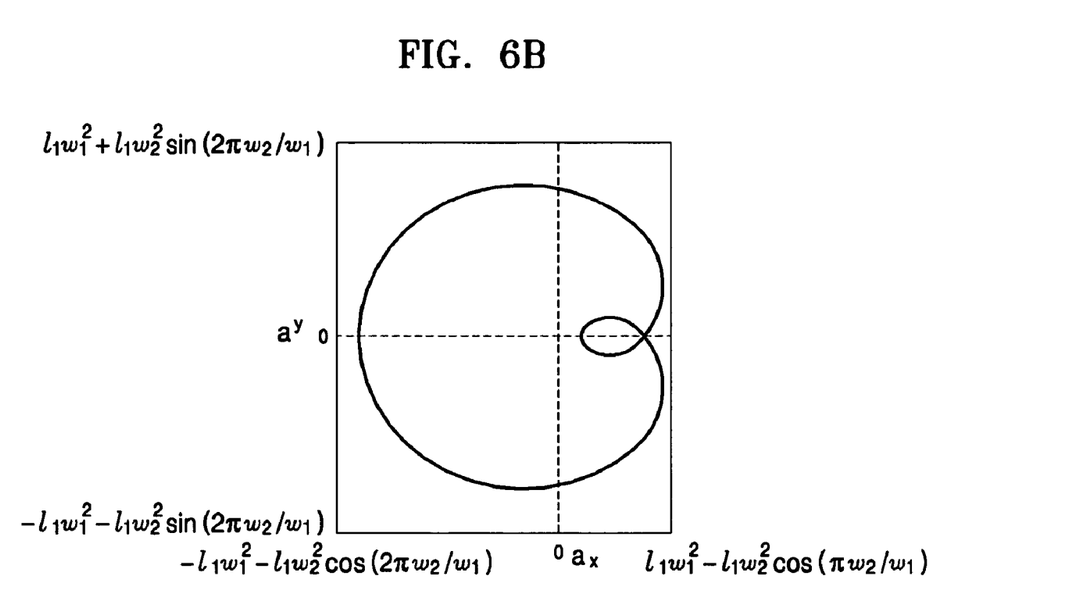
FIG. 6B is a phase diagram for the gravity direction and the horizontal direction components of acceleration, which is symmetric about the axis of the gravity direction component.

When the movement trajectory is modeled as a double pendulum, the acceleration signals in the gravity and horizontal directions show a phase diagram that is asymmetrical with respect to the acceleration axis for the gravity direction component as shown in FIG. 6B.

Accordingly, from the phase diagram of the acceleration in the gravity direction and the horizontal direction, it can be determined whether the movement trajectory is modeled as a single pendulum or a double pendulum, and the wearing location of the sensor unit 10 can be also determined. That is, it can be determined to which part, such as the hand or leg, the sensor unit 10 is attached, or whether the sensor unit 10 is carried in a handbag apart from the human body.

If the wearing location of the sensor unit 10 is detected, the wearing mode is determined at that location by using acceleration values on the space fixed coordinates in operation 22 (FIG. 2). Here, the wearing mode indicates an activity pattern such as walking, running or cycling. The determination is made by referring to the frequency and intensity of the acceleration signal with respect to the wearing location. This is because even though activity patterns may be identical, the acceleration signals vary according to the wearing location of the sensor unit 10. That is, the detected acceleration signals of the sensor unit 10 held in the hand and put in the pocket may be different. Also, preferably, the data processing unit stores acceleration ranges for each activity pattern with respect to the wearing location in order to determine the wearing mode.

When the activity being performed, or wearing mode, is determined, the presence or absence of periodicity in an acceleration signal is determined. Periodicity is determined because the signal of walking, running, or cycling shows periodicity in the gravity direction or in the horizontal direction according to the wearing location of the sensor unit 10.

More specifically, the determination of the activity pattern can be performed by calculating the dynamic parameters of the gravity direction component and horizontal direction component of an acceleration signal.

Figure 7A:
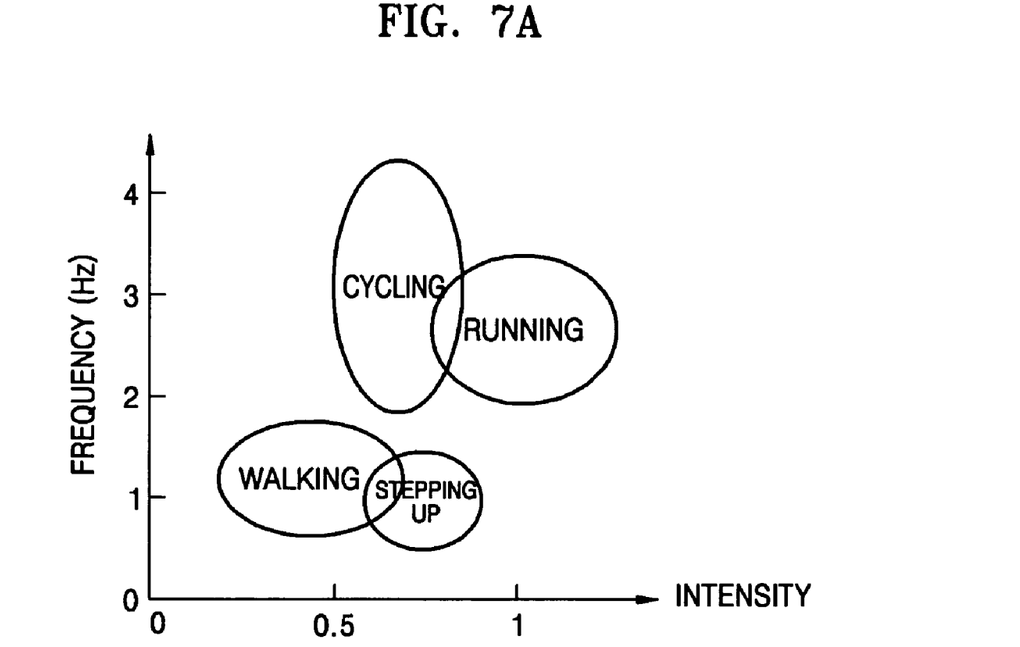
FIGS. 7A and 7B illustrate frequency distributions of the gravity direction and the horizontal direction components of an acceleration signal, respectively, with respect to intensity according to the pattern of activity.
Figure 7B:
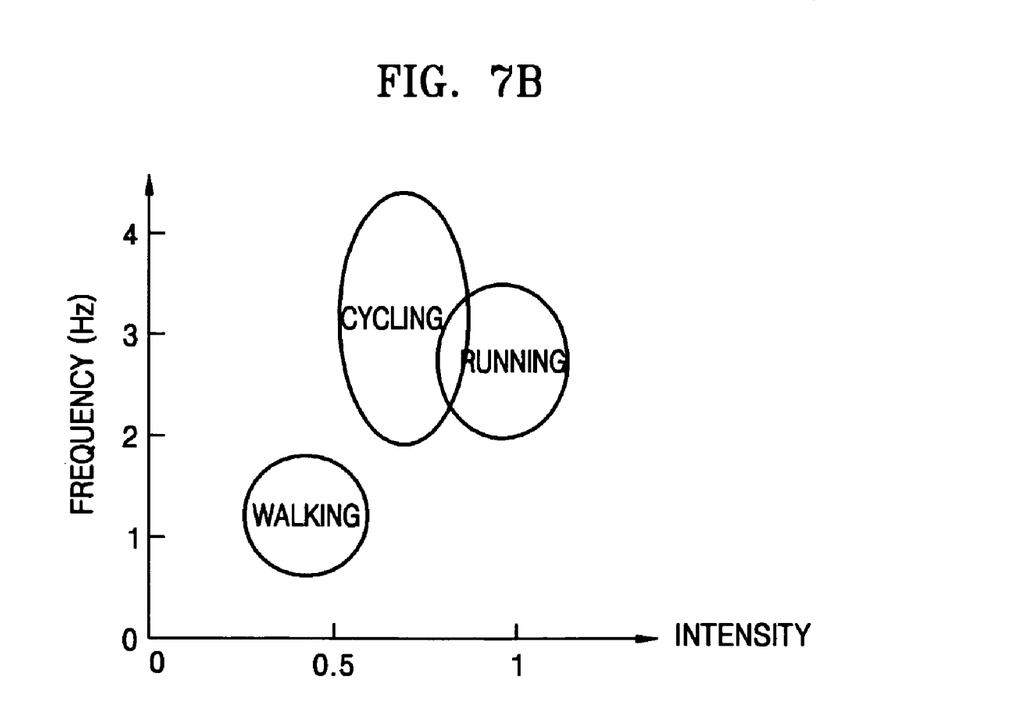

FIGS. 7A and 7B illustrate the frequency distribution of the components of an acceleration signal in the gravity direction and the horizontal direction, respectively, with respect to signal intensity according to the pattern of activity. In a case wherein the movement speed of a leg is measured, the sensor unit 10 is attached on the thigh. Referring to FIGS. 7A and 7B, each unique frequency and intensity area is divided in the gravity direction and horizontal direction, in FIGS. 7A and 7B, respectively, for each type of activity. Similar distribution plots or phase diagrams can be made by replacing the intensity axis with other dynamic parameters such as mean, median, peak, standard deviation, skew, or kurtosis of acceleration for each direction, and a correlation coefficient between each pair of accelerations can be used to classify the physical activity more specifically.

In case there is overlap of more than two activities for given dynamic parameters, a sum of conditional probabilities of dynamic parameters given that an activity occurs will determine the activity pattern such as $$\Sigma_i = \sum_j p(\eta_i \mid \xi_j) p(\xi_j) = \sum_j p(\eta_i \mid \xi_j) \qquad (4)$$

wherein, $\eta_i$: pattern (e.g, rest, walk, jog, run), $\xi_j$: dynamic parameter (e.g, $\sigma_x$, etc), According to equation (4), the activity can be classified by finding the maximum $\Sigma_i$.

Figure 10:
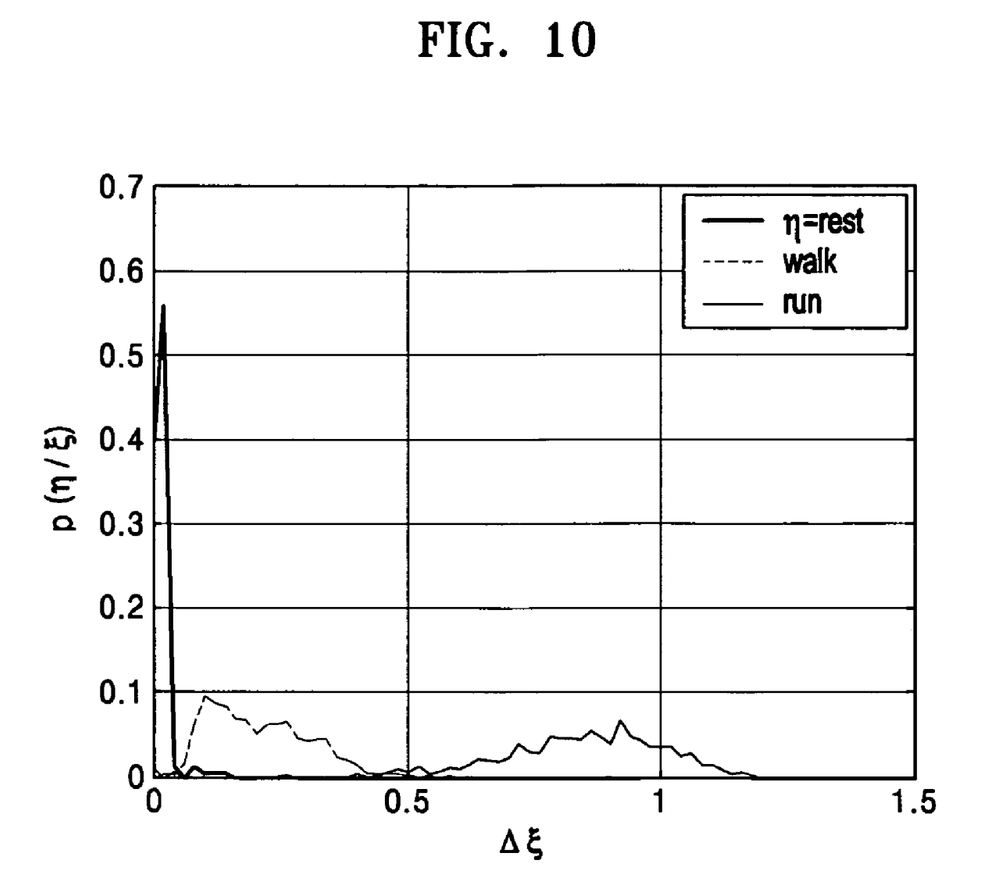
FIG. 10 illustrates an example of conditional probabilities of activity pattern.

FIG. 10 illustrates an example of conditional probabilities of activity pattern. In FIG. 10, the horizontal axis is of standard deviation of $\zeta$. As shown in FIG. 10, each of the activity patterns is distinguished from each other.

The activity pattern and its duration can be provided to the user through the mobile terminal 13. Thus, the user can learn which activity pattern was performed, when it was performed, and for how long.

If the activity pattern is walking or running, the data processing unit 11 again detects the current wearing location of the sensor unit 10. This is to determine whether the wearing location of the sensor unit 10 is changed during the activity. For example, if the location of the sensor unit 10 is changed from the user's hand in the pocket, the acceleration and direction detected by the sensor unit 10 also change, and therefore the operation 21 is performed again to detect the wearing location.

If the activity pattern is determined, the analysis of the determined activity pattern can be performed in operation 23. The analysis of the activity pattern includes calculation of calories consumed by the activity pattern, the number of steps, and the moving distance. In addition, if the gravity direction component of the acceleration value sharply changes while the change in the horizontal direction component is negligible, it is determined that the user has fallen over, and an alarm can be sent through the mobile terminal 13. If it is determined from personal information that the user is advanced in age, an emergency center can be informed of the fall by the mobile terminal 13.

As an example of the analysis of the activity pattern, the process for measuring the consumed calories will now be explained in more detail.

Figure 8A:
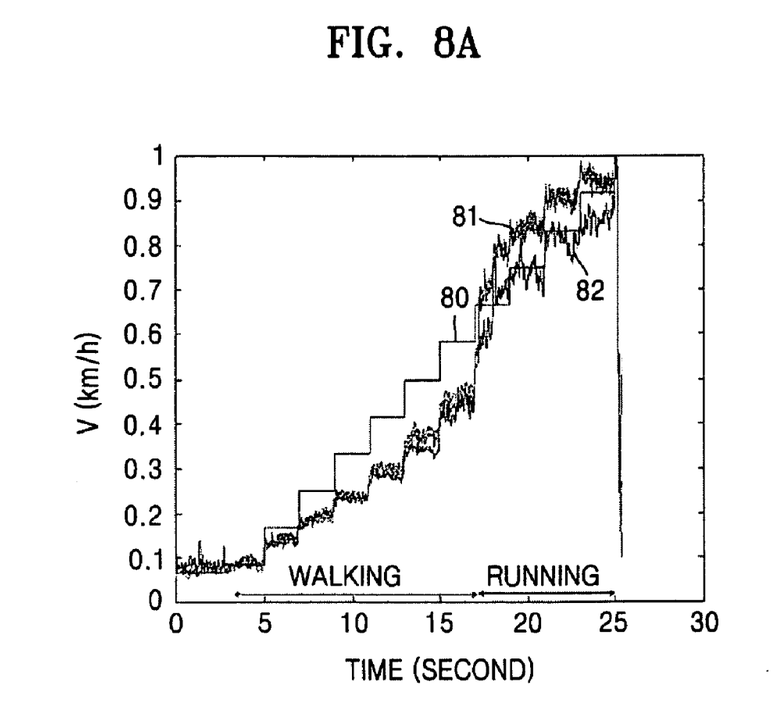
FIG. 8A illustrates values output from an acceleration sensor when speed increases over time.
Figure 8B:
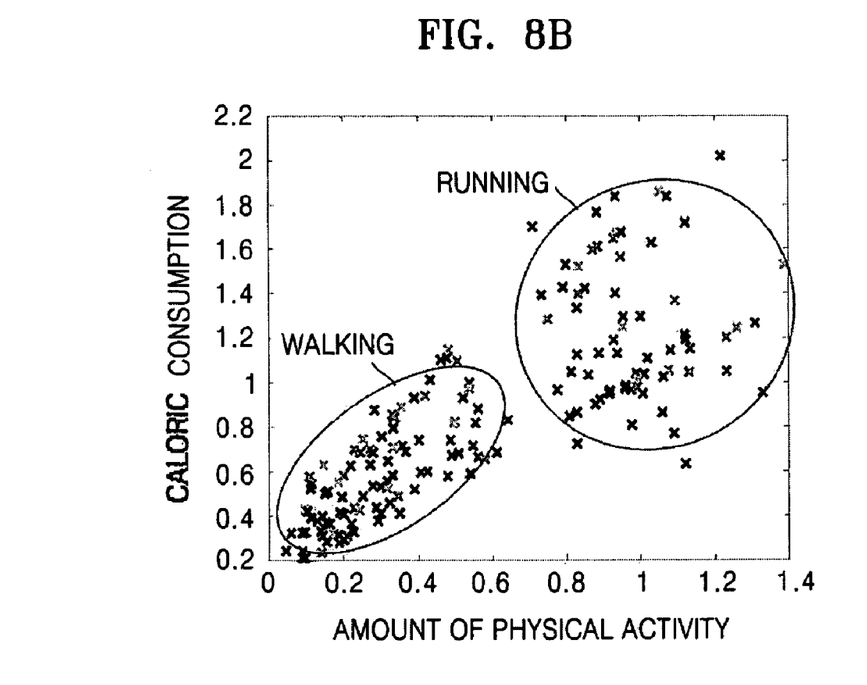
FIG. 8B illustrates the amount of caloric consumption measured with respect to an amount of physical activity for 24 individual users.

FIG. 8A illustrates values output from the acceleration sensor 101 when speed is increased over time. Reference number 80 indicates the speed gradually increasing over time, and reference numbers 81 and 82 show acceleration sensed by different acceleration sensors. Referring to FIG. 8A, the speed of 0.7 km/h or more is regarded as that of running, and it can be seen that the values output from the acceleration sensor 101 change abruptly from those output when the speed is 0.6 km/h. FIG. 8B illustrates the caloric consumption of 24 users, measured with respect to the amount of physical activity. Referring to FIG. 8B, it can be seen that the caloric consumption amount for walking is clearly distinguished from that for running. Also, it can be seen that even in the area for running or walking, the measured amounts have a wide distribution. This distribution occurs because the physical condition of users varies. Accordingly, in an exemplary embodiment of the present invention, the consumed calories are measured with reference to the personal information of the user. The personal information includes at least one of the sex, age, height, and weight of the user. The caloric consumption has a linear relation with respect to the amount of physical activity measured by the acceleration sensor 101, as described by the following equation 4:

$$Calorie = b \times VM + c \qquad (5)$$

$$VM = \sqrt{\sum_{i=x,y,z} \int a_i dt}$$

Here, b and c are constants and $a_i$ is an acceleration signal.

In the equation 4, constants b and c are determined according to the personal information of an individual, and in the present invention, are obtained by applying a known multiple regression analysis method.

As another example of the activity mode, measuring the number of steps will now be explained. Generally, the number of steps is measured by counting the number of times the gravity direction component of the acceleration exceeds a certain value. The number of steps is inclined to be overcounted when the user walks fast while inclined to be undercounted when the use walks slowly. Also, shock noises such as random shocks can be measured incorrectly as steps.

Accordingly, in the present exemplary embodiment, according to the changing range of the gravity direction component of the acceleration, the measuring time and threshold value are adjusted, and after measuring the steps, a locking period is set so that the shock noises are not measured.

Figure 9A:
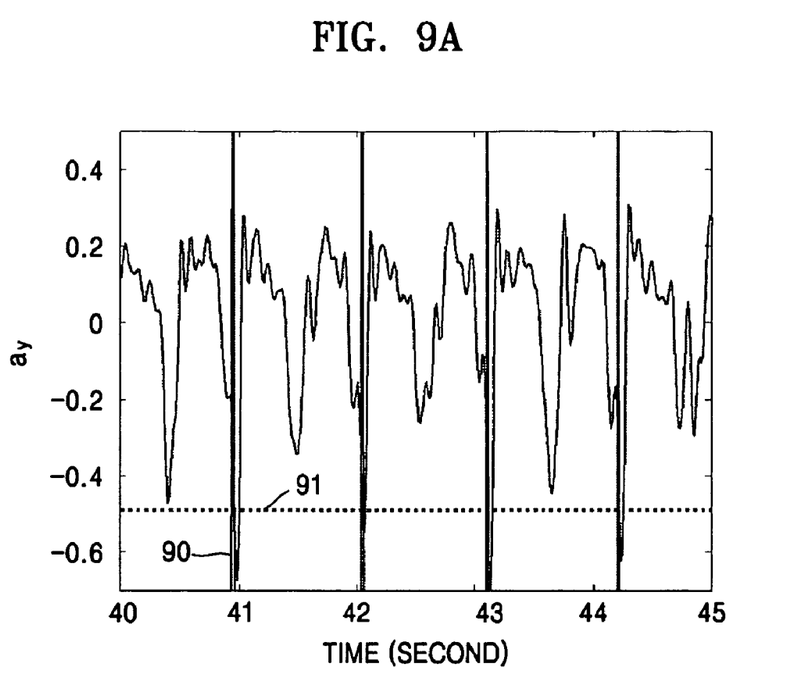
FIGS. 9A and 9B illustrate acceleration components in the gravity direction when a user moves at speeds of 3.0 km/h and 8.5 km/h, respectively.
Figure 9B:
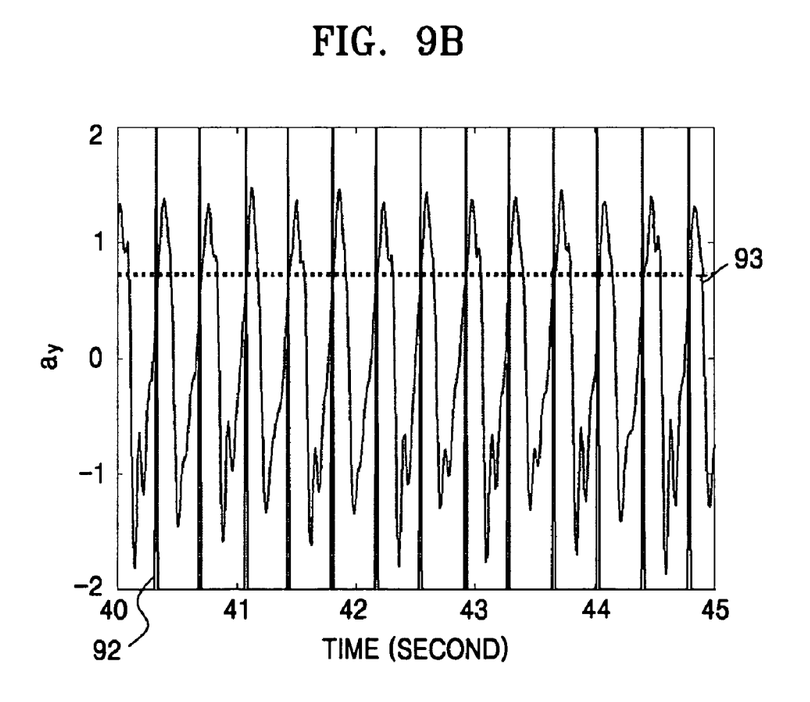

FIGS. 9A and 9B illustrate the gravity direction components of the acceleration when a user moves at speeds of 3.0 km/h and 8.5 km/h, respectively. Reference numbers 90 and 92 each indicate a time for beginning to count the number of steps in FIGS. 9A and 9B, respectively. While reference numbers 91 and 93 indicate threshold speed levels counted by steps, in FIGS. 9A and 9B, respectively.

Referring to FIGS. 9A and 9B, in order to measure the number of steps, it is preferable that with the increasing activity intensity, the counting time interval is shorter and the threshold value is higher. If the number of steps is measured, the moving distance can also be calculated. According to sports medicine, the length of a step of an ordinary person is (height-100 cm), so if the length is multiplied by the number of steps, the moving distance can be calculated.

If the analysis of the activity pattern is performed, the analysis result can be provided to the user through the mobile terminal 13 in operation 24. The result includes current caloric consumption, number of steps, and/or moving distance.

The present invention can also be embodied as computer readable code on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices, and carrier waves (such as data transmission through the internet). The computer readable recording medium can also be distributed over network coupled computer systems so that the computer readable code is stored and executed in a distributed fashion. Also, functional programs, code, and code segments for accomplishing the present invention can be easily construed by programmers skilled in the art to which the present invention pertains.

According to the present invention, by detecting the location on which the sensor is attached, and monitoring the activity pattern of the user with reference to the detected location, the activity pattern of the user can be monitored without limiting the wearing location of the sensor.

Also, by measuring the activity pattern, the elapsed time, the caloric consumption of the activity, the number of steps, or the moving distance, information on the amount of physical activity can be provided to the user.

Furthermore, if the user falls over, then if necessary, the mobile terminal can notify an emergency center.

While the present invention has been particularly shown and described with reference to exemplary embodiments thereof, it will be understood by those of ordinary skill in the art that various changes in form and details may be made therein without departing from the spirit and scope of the present invention as defined by the following claims. The exemplary embodiments should be considered in a descriptive sense only and not for purposes of limitation. Therefore, the scope of the invention is defined not by the detailed description of the invention but by the appended claims, and all differences within their scope will be construed as being included in the present invention.

What is claimed is:

1. A method for monitoring an activity pattern comprising:
    sensing an inertia movement signal according to a movement of a user using a sensor unit attached to the user;
    detecting a direction of the sensor unit from the inertia movement signal;
    detecting a wearing location of the sensor unit, by using the inertia movement signal and the direction; and
    determining the activity pattern of the user from the inertia movement signal by reflecting the wearing location.

2. The method of claim 1, wherein the direction is detected from a DC component of the inertia movement signal by obtaining a roll angle and a pitch angle of the sensor unit with respect to a planar surface of the sensor unit.

3. The method of claim 2, wherein the inertia movement signal is compensated for the direction by multiplying an AC component of the inertia movement signal by a rotational transform matrix defined as the pitch angle and the roll angle.

4. The method of claim 2, wherein the sensor unit comprises a tilt sensor and the roll angle and the pitch angle are detected by the tilt sensor.

5. The method of claim 2, wherein the sensor unit comprises a terrestrial magnetism sensor, and the direction is detected by further obtaining a yaw angle swept by the terrestrial magnetism sensor from a reference line on a planar surface.

6. The method of claim 2, wherein the sensor unit further includes a gyroscope and the direction is detected by further obtaining an integration of angular speed in a horizontal plane.

7. The method of claim 1, wherein detecting the wearing location comprises:
by using the direction, transforming the inertia movement signal output from the sensor unit into an inertia movement signal in space fixed coordinates; and
obtaining the wearing location of the sensor unit from differences between signal patterns of the transformed inertia movement signal according to locations of the sensor unit.

8. The method of claim 1, wherein determining the activity pattern comprises:
extracting dynamic parameters of inertia movement at a predetermined sensor unit location; and
determining the activity pattern from a distribution of the values of extracted dynamic parameters.

9. The method of claim 1, further comprising:
analyzing the activity pattern according to the determined activity pattern.

10. The method of claim 9, further comprising:
if the activity pattern is determined to be walking or running, detecting a second wearing location of the sensor unit; and
if the second detected wearing location is changed from a previous wearing location, analyzing again the activity pattern at the second detected wearing location.

11. The method of claim 10, wherein in analyzing the activity pattern, at least one of a caloric consumption during the activity, a number of steps, and a moving distance is measured by using the inertia movement signal.

12. The method of claim 11, wherein the caloric consumption is measured by obtaining a vector magnitude of an integrated acceleration signal and regression coefficients of caloric consumption contain physical information including at least one of a height, a sex, an age, and a weight of the user.

13. The method of claim 11, wherein the number of steps is counted when a gravity direction component of the inertia movement signal is equal to or greater than a threshold, and the threshold is adjusted in proportion to a changing range of the gravity direction component.

14. An apparatus for monitoring an activity pattern comprising:
a sensor unit attached to a user, which senses an inertia movement signal according to a movement of the user; and
a data processing unit which detects a direction of the sensor unit by using the inertia movement signal, and which detects a wearing location of the sensor unit by using the inertia movement signal and the direction, and which determines the activity pattern of the user from the inertia movement signal by reflecting the wearing location.

15. The apparatus of claim 14, wherein the sensor unit further comprises:
at least one of a terrestrial magnetism sensor and a gyroscope, which detect a direction directed by terrestrial magnetism on a planar surface,
wherein the data processing unit detects the wearing location of the sensor unit by using a direction further including the direction detected by the terrestrial magnetism sensor or the gyroscope, and the inertia movement signal.

16. The apparatus of claim 14, wherein the data processing unit measures at least one of a caloric consumption, a number of steps, and a moving distance according to the determined activity pattern.

17. The apparatus of claim 14, further comprising:
a mobile terminal carried by the user and displaying the determined and measured results output from the data processing unit, wherein the sensor unit and the data processing unit are embedded in the mobile terminal.

* * * * *